United States Patent
Cheng et al.

(10) Patent No.: US 12,036,382 B2
(45) Date of Patent: Jul. 16, 2024

(54) CARRYING CASE FOR AN ADD-ON DEVICE OF A MEDICAMENT DELIVERY DEVICE

(71) Applicant: SHL MEDICAL AG, Zug (CH)

(72) Inventors: Yu-Cheng Cheng, New Taipei (TW); Daniel Benjamin De Waard, North Ringwood (AU)

(73) Assignee: SHL Medical AG, Zug (CH)

( * ) Notice: Subject to any disclaimer, the term of this patent is extended or adjusted under 35 U.S.C. 154(b) by 893 days.

(21) Appl. No.: 16/976,851

(22) PCT Filed: Feb. 18, 2019

(86) PCT No.: PCT/EP2019/053919
§ 371 (c)(1),
(2) Date: Aug. 31, 2020

(87) PCT Pub. No.: WO2019/170401
PCT Pub. Date: Sep. 12, 2019

(65) Prior Publication Data
US 2020/0405946 A1    Dec. 31, 2020

(30) Foreign Application Priority Data
Mar. 8, 2018   (EP) .................................. 18160653

(51) Int. Cl.
*A61M 5/00*   (2006.01)
(52) U.S. Cl.
CPC ..... *A61M 5/003* (2013.01); *A61M 2205/3368* (2013.01); *A61M 2205/3553* (2013.01); *A61M 2205/3633* (2013.01); *A61M 2205/583* (2013.01); *A61M 2205/8243* (2013.01); *A61M 2205/8256* (2013.01)

(58) Field of Classification Search
CPC .. A61M 2205/3368; A61M 2205/3553; A61M 2205/3633; A61M 2205/583; A61M 205/8243; A61M 2205/8256
USPC ........................................................ 455/500
See application file for complete search history.

(56) References Cited

U.S. PATENT DOCUMENTS

| 9,980,140 | B1 * | 5/2018 | Spencer ................ H04W 12/02 |
| 11,238,133 | B1 * | 2/2022 | Brewer ............. A61M 5/14248 |
| 2007/0239116 | A1 | 10/2007 | Follman |
| 2010/0160759 | A1 * | 6/2010 | Celentano ............. A61M 5/172 600/365 |

(Continued)

FOREIGN PATENT DOCUMENTS

| EP | 2357013 A1 | 8/2011 |
| EP | 2756856 A1 | 7/2014 |

(Continued)

OTHER PUBLICATIONS

International Search Report and Written Opinion for Int. App. No. PCT/EP2019/053919, completed Mar. 7, 2019.

*Primary Examiner* — April G Gonzales
(74) *Attorney, Agent, or Firm* — McDonnell Boehnen Hulbert & Berghoff LLP

(57) ABSTRACT

A carrying case for an add-on device of a medicament delivery device is presented where the carrying case has an add-on device holder configured to hold the add-on device, an energy storage device, and a charging device configured to wirelessly electrically charge the add-on device from the energy storage device when the add-on device is held by the add-on device holder.

12 Claims, 1 Drawing Sheet

(56) References Cited

U.S. PATENT DOCUMENTS

| | | | | |
|---|---|---|---|---|
| 2011/0295215 A1* | 12/2011 | Nielsen | ................. | G16H 20/17 |
| | | | | 604/257 |
| 2013/0331790 A1* | 12/2013 | Brown | ............... | H01R 13/5224 |
| | | | | 604/151 |
| 2015/0190577 A1* | 7/2015 | Shaanan | ........... | A61M 5/31575 |
| | | | | 604/209 |
| 2015/0265780 A1 | 9/2015 | Pesach | | |
| 2016/0074587 A1* | 3/2016 | Searle | ............... | A61M 5/16804 |
| | | | | 604/189 |
| 2017/0199985 A1* | 7/2017 | Mazlish | ............ | A61M 5/14244 |
| 2017/0286638 A1* | 10/2017 | Searle | ................... | G16H 40/63 |
| 2018/0200439 A1* | 7/2018 | Mazlish | ............. | A61M 5/1723 |
| 2018/0200441 A1* | 7/2018 | Desborough | ...... | A61B 5/14532 |

FOREIGN PATENT DOCUMENTS

| | | |
|---|---|---|
| WO | 2011/117404 A2 | 9/2011 |
| WO | 2013/065055 A1 | 5/2013 |
| WO | 2014/064691 A2 | 5/2014 |
| WO | 2014/097055 A1 | 6/2014 |
| WO | 2018/136901 A1 | 7/2018 |

\* cited by examiner

CARRYING CASE FOR AN ADD-ON DEVICE OF A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2019/053919 filed Feb. 18, 2019, which claims priority to European Patent Application No. 18160653.4 filed Mar. 8, 2018. The entire disclosure contents of these applications are herewith incorporated by reference into the present application.

TECHNICAL FIELD

The present disclosure generally relates to a carrying case for medical applications.

BACKGROUND

Patients dependent upon regular medication may find it cumbersome to carry with them their medicaments. For example, diabetic patients who use insulin pens and move between different locations may experience problems carrying the insulin pen and other related supplies like pen needles. Carrying cases are therefore available, allowing the patient to collect medical items therein. Problems may however arise also when patients use carrying cases. For example, diabetic patients may sometimes after use forget to put the insulin pen back into the carrying case. A patient may thus potentially carry the case without the insulin pen in it when insulin is to be administered.

Insulin pens today may be provided with electronics, e.g. to register the time of medicament administration and the dosage, and a battery for powering the electronics. It may in this case be convenient to be able to charge the battery when the insulin pen is arranged in the carrying case. U.S. Pat. No. 8,398,602 B2 discloses a carrying case for a pharmaceutical injection device. The carrying case includes a case unit and an electric charging device. The case unit accommodates the pharmaceutical injection device. The electrical charging device is mounted in the case unit and includes an electric charging terminal electrically connectable to the pharmaceutical injection device. The electric charging device electrically charges the pharmaceutical injection device.

SUMMARY

Insulin pens without the capabilities of insulin pens comprising electronics may be provided with an add-on device, sometimes also referred to as a supplementary device. The add-on device is configured to be attached to the insulin pen. The add-on device comprises an energy storage unit such as a battery, and electronics, powered by the battery, able to register use data for the insulin pen to which it is attached, thus compensating for the lack of these features in the insulin pen. In particular, the add-on device interfaces with the insulin pen, and may be provided with means that detect dosage selection and/or activation of the insulin pen. For example, the add-on device may comprise one or more sensors that detect e.g. mechanical movement or vibration in the insulin pen, and thereby registers a medicament administration and/or dosage. Hereto, add-on devices may contain important data relating to the insulation pen, and about how the user utilises the insulin pen.

In view of the above, a general object of the present disclosure is to provide a carrying case which solves or at least mitigates problems of the prior art.

There is hence according to a first aspect of the present disclosure provided a carrying case for an add-on device of a medicament delivery device, the carrying case comprising: an add-on device holder configured to hold the add-on device, an energy storage device, and a charging device configured to wirelessly electrically charge the add-on device from the energy storage device when the add-on device is held by the add-on device holder.

An effect obtainable thereby is that the add-on device may be charged when stored in the carrying case. The add-on device may for example be stored in the carrying case between medicament administrations. It may thereby be ensured that the add-on device is charged and able to register administration-related data in conjunction with medicament administration.

The wireless electrical charging may for example involve inductive power transfer, i.e. by inductive coupling, or conductive power transfer, i.e. by conductive coupling.

The energy storage device may be a battery.

One embodiment comprises near-field wireless communication circuitry configured to communicate with the add-on device.

According to one embodiment the near-field wireless communication circuitry is configured to act as an initiator and generate a radio frequency, RF, electromagnetic field to power wireless communication from the add-on device. The add-on device will thereby not need to use its own power for the purpose of wireless communication with the carrying case.

One embodiment comprises far-field wireless communication circuitry, wherein the far-field wireless communication circuitry is configured to transmit data received from the add-on device via the near-field wireless communication circuitry to a remote server. The data relating to medicament administration collected by the add-on device may thus be transmitted to a remote server for further use. Such data may for example include administration/injection time and/or the medicament dose. The add-on device will thus not have to use its own power for this purpose.

The carrying case may be configured to transmit the data automatically to the remote server. Alternatively, data transmission could be user-initiated.

According to one embodiment the add-on device holder comprises a first recess configured to receive the add-on device. This facilitates charging of the add-on device, since it may be better fixated with respect to the charging device. Additionally, a well-defined position is provided for embodiments with near-field wireless communication circuitry, ensuring better connectivity.

One embodiment comprises a medicament delivery device holder configured to hold the medicament delivery device. The medicament delivery device to which the add-on device is configured to be connected may thus also be received by the carrying case. This may facilitate handling of the items used for medicament delivery.

The medicament delivery device holder and the add-on device holder may be arranged relative to each other such that the medicament delivery device in an assembled state with the add-on device holder may be held by the medicament delivery device holder and the add-on device holder. Alternatively, the add-on device holder may be arranged such that the add-on device has to be removed from the medicament delivery device in order to hold the add-on device, and the medicament delivery device holder may be arranged such that the medicament delivery device can only be held without the add-on device attached to it.

According to one embodiment the medicament delivery device holder comprises a second recess configured to receive the medicament delivery device.

One embodiment comprises a medicament delivery device detector configured to detect the presence of the medicament delivery device when held by the medicament delivery device holder.

One embodiment comprises a first indicator configured to indicate to a user that the medicament delivery device is missing from the carrying case in the event that the medicament delivery device detector after a predetermined amount of time fails to detect the presence of the medicament delivery device in the medicament delivery device holder. A user may thereby be made aware of whether the carrying case contains the medicament delivery device. The risk of a user forgetting to bring the medicament delivery device in the carrying case may thereby be reduced.

According to one example the indicator is configured to indicate that the medicament delivery device is missing in the event that the carrying case is being closed, or has just been closed, and the medicament delivery device detector fails to detect the presence of the medicament delivery device in the medicament delivery device holder. A user may thereby be made aware that the medicament delivery device is missing from the carrying case when closing the carrying case, or just after the carrying case has been closed. The risk of a user forgetting to bring the medicament delivery device with the carrying case can hence be reduced.

One embodiment comprises a temperature sensor configured to detect a temperature inside the carrying case, and a second indicator configured to indicate to a user in case a detected temperature is above a predetermined threshold value, above which a medicament contained in the medicament delivery device could become damaged. A user may thereby be notified if a temperature in the carrying case exceeds a safe limit.

One embodiment comprises a display device configured to display add-on device-related information. Add-on device related information may for example be data received from an add-on device via near-field wireless communication circuitry.

The display device may for example comprise an E-ink display. E-ink displays consume less power than many other types of displays.

The display device may according to one example be a touch display. The user may thereby be able to interact with the carrying case. The user may for example be able to access data received from the add-on device, such as administration/injection time, dosage, and/or historical records regarding medicament administration.

According to one embodiment the display device is configured to display a low energy level of the energy storage device and/or indicate that a temperature inside the carrying case is above a predetermined threshold value and/or indicate that the medicament delivery device is missing from the carrying case.

The first indicator and/or the second indicator may for example be implemented as the display device. The display device may thus for example be configured to indicate to a user in case the medicament delivery device detector after a predetermined amount of time fails to detect the presence of the medicament delivery device in the medicament delivery device holder, and/or to indicate that a detected temperature is above a predetermined threshold value, above which a medicament contained in the medicament delivery device could become damaged.

The first indicator and/or the second indicator may alternatively or additionally comprise for example a sound module, configured to create different sounds based on the type of information that is to be provided to a user.

According to one embodiment the carrying case is made of a thermally insulating material. The temperature inside the carrying case will thereby be less sensitive to ambient temperature changes and protect the medicament contained in a medicament delivery device held by the carrying case.

There is according to a second aspect of the present disclosure provided a medical system comprising: an add-on device for a medicament delivery device, a carrying case according to the first aspect, and a remote server configured to communicate wirelessly with the carrying case.

According to one embodiment the medicament delivery device is an insulin injection device, e.g. an insulin pen.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
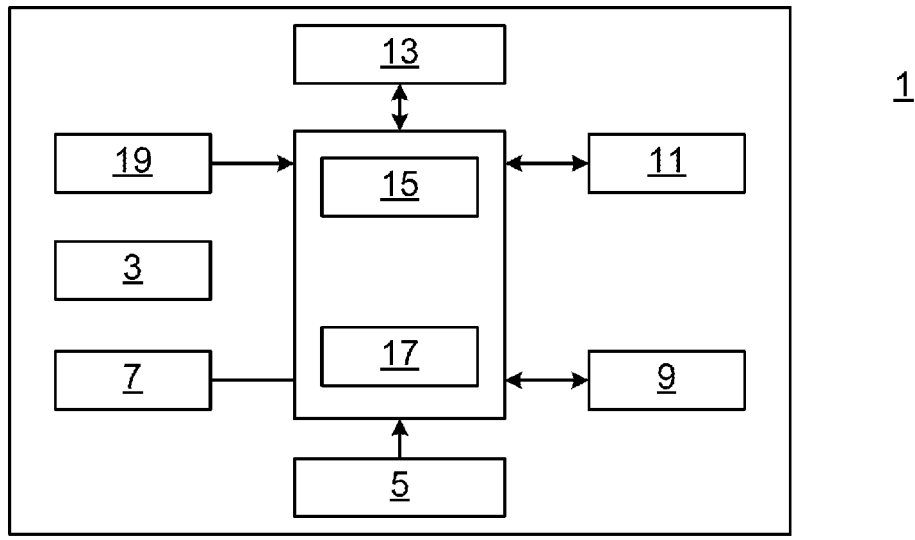
FIG. 1 is a block diagram of an example of a carrying case for an add-on device.

FIG. 1 shows an example of a carrying case for an add-on device configured to be used with a medicament delivery device.

The exemplified carrying case 1 comprises an add-on device holder 3. The add-on device holder 3 is configured to hold an add-on device. The add-on device holder 3 may for example comprise a dock for docking the add-on device and/or a recess for receiving the add-on device.

The carrying case 1 is configured to be opened and to be closed. Hereto, the carrying case 1 has a closed space when the carrying case is closed, configured to accommodate the add-on device. In an open state of the carrying case 1, a user may place an add-on device in the add-on device holder 3 or remove the add-on device from the add-on device holder 3.

The carrying case 1 comprises an energy storage device 5. The energy storage device 5 may for example comprise a battery. The battery is preferably a rechargeable battery. To this end, the carrying case 1 may comprise means for connecting it to a power outlet to thereby charge the battery. Alternatively, the battery could be removable, and charged when removed from the carrying case 1. According to another alternative, the carrying case 1 could be configured to enable wireless electrical charging of the battery.

The carrying case 1 furthermore comprises a charging device 7. The charging device 7 is connected to the energy storage device 5. The energy storage device 5 is configured to power the charging device 7. The charging device 7 is configured to wirelessly electrically charge the add-on device when the add-on device is held by the add-on device holder 3. Power charging can thus be initiated when the add-on device is placed in the add-on device holder 3.

The charging device 7 may for example be an inductive power charging device or a conductive power charging device.

The exemplified carrying case 1 comprises near-field wireless circuitry 9. The near-field wireless circuitry 9 is configured to provide communication between the carrying case 1 and an add-on device. The near-field wireless communication circuitry may be configured to act as an initiator and generate an RF electromagnetic field to power wireless communication from the add-on device. The communications circuit of the add-on device may thus be a passive communications circuit, configured to be powered by the near-field wireless communication circuitry 9.

By means of the near-field wireless circuitry 9, the carrying case 1 is able to receive data from an add-on device. This data may typically comprise medicament administration related information such as administration time, dosage, whether the administration was carried out correctly, etc.

The carrying case 1 may further comprise a first indicator and/or a second indicator for indicating carrying-case related information. In the following, both of these indicators will be exemplified by a display device 11. The display device 11 may for example comprise an e-ink display. The display device 11 may be configured to display data received by the carrying case 1 from an add-on device via the near-field wireless circuitry 9. The display device 11 may according to one variation be configured to allow a user to interact with the carrying case 1. The display device 11 may thus form part of a user interface of the carrying case 1. The display device 11 may for example enable touch interaction. A user may thereby for example be able to obtain information about administration history, and/or to select user settings for the carrying case 1.

The display device 11 may be configured to display that the energy storage device 5, in particular the battery, has a low energy level.

The carrying case 1 may comprise far-field wireless communications circuitry 13 configured to transmit data to a remote server. The far-field wireless communications circuitry may in particular be configured to transmit data received from the add-on device via the near-field wireless communication circuitry 9. The far-field wireless communication circuitry 13 may for example support a cellular radio access technology such as 3G, 4G or 5G, and/or Wireless LAN (WLAN).

The carrying case 1 may also comprise a storage medium 17 and processing circuitry 15 configured to communicate with the storage medium 17. The processing circuitry 15 may be configured to coordinate and control operation carrying case 1, e.g. of the display device 11, of the near-field wireless communication circuitry 9, of the charging device 7, and of the far-field wireless communications circuitry 13.

The processing circuitry 15 may use any combination of one or more of a suitable central processing unit (CPU), multiprocessor, microcontroller, digital signal processor (DSP), application specific integrated circuit (ASIC), field programmable gate arrays (FPGA) etc., capable of executing any herein disclosed operations concerning charging, near and far-field data communication, temperature detection, medicament delivery device detection, etc.

The storage medium 13 may for example be embodied as a memory, such as a random access memory (RAM), a read-only memory (ROM), an erasable programmable read-only memory (EPROM), or an electrically erasable programmable read-only memory (EEPROM) and more particularly as a non-volatile storage medium of a device in an external memory such as a USB (Universal Serial Bus) memory or a Flash memory, such as a compact Flash memory.

The carrying case 1 may also comprise a medicament delivery device holder configured to hold a medicament delivery device. The medicament delivery device holder may for example comprise a dock for docking the medicament delivery device, and/or a recess for receiving the medicament delivery device, or a strap for holding the medicament delivery device.

The carrying case 1 may preferably comprise a thermally insulating material if provided with a medicament delivery device holder. In particular, an outer wall, inner wall, or cover of the carrying case 1 may comprise the thermally insulating material. This ensures that when the carrying case 1 is closed, the internal temperature in the closed space can be maintained. Better temperature control of a medicament contained in the medicament delivery device may hence be provided when stored in the carrying case 1.

The carrying case 1 may comprise a medicament delivery device detector configured to detect the presence of the medicament delivery device when held by the medicament delivery device holder. The medicament delivery device detector may for example be a mechanical, electromechanical, electronic, or optical sensor.

The processing circuitry 15 may be configured to determine that that the medicament delivery device is missing from the carrying case in the event that the medicament delivery device detector after a predetermined amount of time fails to detect the presence of the medicament delivery device in the medicament delivery device holder. Further, the display device 11 may be configured to indicate that the medicament delivery device is missing. Alternatively, or additionally, the carrying case 1 may comprise an aural indicator or a sound module, e.g. the first indicator may comprise an aural indicator/sound module, configured to aurally indicate that that the medicament delivery device is missing from the carrying case 1.

The carrying case 1 may comprise a temperature sensor 19 configured to detect a temperature inside the carrying case 1. The display device 11 may be configured to indicate that a temperature detected by the temperature sensor 19 is above a predetermined threshold value. The predetermined threshold value may for example be a temperature above which there is risk that a medicament contained in the medicament delivery device could become damaged.

Figure 2:
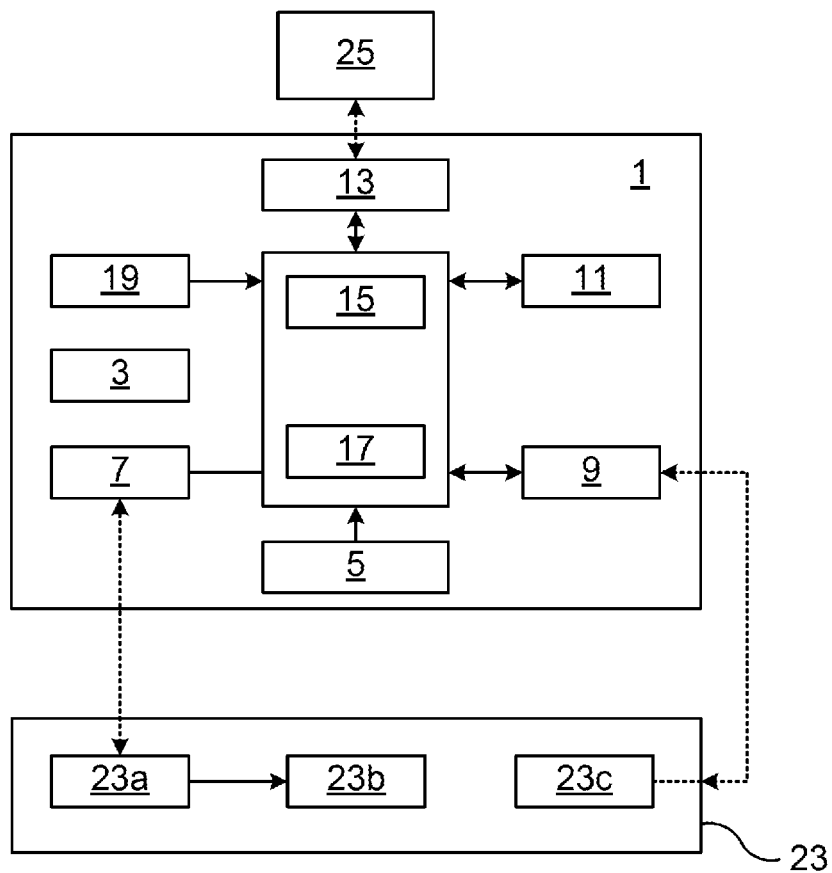
FIG. 2 depicts a block diagram of a medical system comprising a carrying case such as carrying case in FIG. 1.

FIG. 2 shows a medical system 21. The medical system 21 comprises a carrying case 1, an add-on device 23 configured to be assembled with a medicament delivery device, and a remote server 25.

The add-on device 23 comprises a charging unit 23*a* configured to inductively or conductively interact with the charging device 7 of the carrying case 1. The add-on device 23 furthermore comprises a rechargeable battery 23*b* connected to the charging unit 23*a* for electrical charging thereof.

The add-on device 23 furthermore comprises a communications circuit 23*c* configured to communicate wirelessly with the carrying case 1 via the near-field wireless communication circuitry 9. The communications circuit 23*c* may be a passive communications circuit configured to be powered by the near-field wireless communication circuitry 9.

The add-on device 23 may furthermore comprise one or more sensors configured to detect dosage and/or medicament administration time, for example, and a storage medium for storing data relating to detected dosage and/or medicament administration time. The communications circuit 23*c* may be configured to transmit this data to the near-field wireless communication circuitry 9 of the carrying case 1.

The remote server 25 is configured to wirelessly communicate with the carrying case 1. In particular, the far-field wireless communication circuitry 13 of the carrying case 1 is configured to transmit data obtained from the add-on device 23 to the remote server 25. The remote server 25 may form part of a cloud service and may comprise a data base for storing data received from the carrying case 1. The remote server 25 may be able to receive data relating to dosage and administration times from a plurality of different carrying cases 1, e.g. from different users.

A typical use of the carrying case 1 may be as follows. A user may place the add-on device 23 and a medicament delivery device inside the carrying case 1 for carrying these between two locations. When the user is to administer medication, the medicament delivery device and the add-on device 23 is removed from the carrying case 1. The user may then set the dosage on the medicament delivery device and administer the medicament with the add-on device 23 attached to the medicament delivery device. The add-on device 23 may then register the dose and the time of medicament administration, as detected by the add-on device 23. The user may afterwards place the medicament delivery device and the add-on device 23 in the carrying case 1. The carrying case 1 detects that the add-on device 23 has been placed in the add-on device holder 3 and wireless charging of the battery 23*b* of the add-on device 23 is initiated. Furthermore, the data collected by the add-on device 23 during medicament administration is transmitted by the communications circuitry 23*c* to the carrying case 1. This transmission of data may for example be automatic and initiated by the near-field wireless communication circuitry 9 in response to the add-on device 23 being docked in the carrying case 1. Alternatively, the transmission may be user-initiated, for example via the display device 11.

When the carrying case 1 has received the data, the user may view the data via the display device 11. The carrying case 1 may be configured to automatically transmit the data via the far-field wireless communication circuitry 13 to the remote server 25. Alternatively, a use may be able to initiate this far-field wireless transmission for example by means of user interaction via the display device 11.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A carrying case for an add-on device of a medicament delivery device, the carrying case comprising:

an add-on device holder configured with a first recess to receive and hold the add-on device;

a medicament delivery device holder configured with a second recess to receive and hold the medicament delivery device, wherein the add-on device must be removed from the medicament delivery device for the add-on device holder to hold the add-on device in the first recess, and wherein the add-on device must be removed from the medicament delivery device for the medicament delivery holder to hold the add-on device in the second recess;

an energy storage device; and a charging device configured to wirelessly electrically charge the add-on device from the energy storage device when the add-on device is held by the add-on device holder in the first recess.

2. The carrying case as claimed in claim 1, comprising near-field wireless communication circuitry configured to communicate with the add-on device.

3. The carrying case as claimed in claim 2, wherein the near-field wireless communication circuitry is configured to act as an initiator and generate a radio frequency, RF, electromagnetic field to power wireless communication from the add-on device.

4. The carrying case as claimed in claim 2, comprising far-field wireless communication circuitry, wherein the far-field wireless communication circuitry is configured to transmit data received from the add-on device via the near-field wireless communication circuitry to a remote server.

5. The carrying case as claimed in claim 1, comprising a medicament delivery device detector configured to detect the presence of the medicament delivery device when held by the medicament delivery device holder.

6. The carrying case as claimed in claim 5, comprising a first indicator configured to indicate to a user that the medicament delivery device is missing from the carrying case in the event that the medicament delivery device detector after a predetermined amount of time fails to detect the presence of the medicament delivery device in the medicament delivery device holder.

7. The carrying case as claimed in claim 1, comprising a temperature sensor configured to detect a temperature inside the carrying case, and a second indicator configured to indicate to a user in case a detected temperature is above a predetermined threshold value, above which a medicament contained in the medicament delivery device could become damaged.

8. The carrying case as claimed in claim 1, comprising a display device configured to display add-on device-related information.

9. The carrying case as claimed in claim 8, wherein the display device is configured to display a low energy level of the energy storage device and/or indicate that a temperature inside the carrying case is above a predetermined threshold value and/or indicate that the medicament delivery device is missing from the carrying case.

10. The carrying case as claimed in claim 1, wherein the carrying case is made of a thermally insulating material.

11. A medical system comprising:

an add-on device for a medicament delivery device, a carrying case as claimed in claim 1, and a remote server configured to communicate wirelessly with the carrying case.

12. The medical system as claimed in claim 11, wherein the medicament delivery device is an insulin injection device.

* * * * *